(12) United States Patent
Kimmel

(10) Patent No.: US 7,421,398 B2
(45) Date of Patent: Sep. 2, 2008

(54) SYSTEM AND METHOD FOR IMPLEMENTING HEALTHCARE FRAUD COUNTERMEASURES

(76) Inventor: Scott T. Kimmel, 3650 N. Federal Hwy., Suite 201, Pompano Beach, FL (US) 33064

( * ) Notice: Subject to any disclaimer, the term of this patent is extended or adjusted under 35 U.S.C. 154(b) by 0 days.

(21) Appl. No.: 11/688,209

(22) Filed: Mar. 19, 2007

(65) Prior Publication Data

US 2007/0260484 A1 Nov. 8, 2007

Related U.S. Application Data

(63) Continuation of application No. 10/348,931, filed on Jan. 22, 2003, now Pat. No. 7,209,886.

(51) Int. Cl.
G06F 19/00 (2006.01)
(52) U.S. Cl. .................... 705/3; 705/2; 435/5
(58) Field of Classification Search .......... 705/2, 705/3
See application file for complete search history.

(56) References Cited

U.S. PATENT DOCUMENTS

| 5,845,255 A * | 12/1998 | Mayaud ................ 705/3 |
| 5,876,926 A * | 3/1999 | Beecham .............. 435/5 |
| 5,930,804 A * | 7/1999 | Yu et al. ............. 707/104.1 |
| 2002/0138306 A1* | 9/2002 | Sabovich ............. 705/3 |
| 2003/0093298 A1* | 5/2003 | Hernandez et al. ...... 705/2 |
| 2004/0260666 A1* | 12/2004 | Pestotnik et al. ....... 706/46 |

* cited by examiner

Primary Examiner—C. Luke Gilligan
Assistant Examiner—R. David Rines

(57) ABSTRACT

A method of discouraging healthcare fraud in conjunction with providing a health care service to a patient in which the patient provides a biometric signature. An event record is created where the event record creates an association between the biometric signature, a patient identifier, and location information indicating a location at which the biometric signature is obtained. The event record is stored in a central data store and can be later retrieved to verify the patient was present at the location.

22 Claims, 9 Drawing Sheets

| RECORD # | PATIENT ID | REFERENCE FINGERPRINT MINUTIA |
|---|---|---|
| 1 | PROVIDER ID | TIME STAMP |
| 2 | PROVIDER ID | TIME STAMP |
| 3 | PROVIDER ID | TIME STAMP |
| ... | ... | ... |
| N | PROVIDER ID | TIME STAMP |

| RECORD # | ACCESS LOG | |
|---|---|---|
| 2 | ACCESSOR ID | ACCESS METADATA |
| 1 | ACCESSOR ID | ACCESS METADATA |
| ... | ... | ... |
| 2 | ACCESSOR ID | ACCESS METADATA |

ABSTRACT# SYSTEM AND METHOD FOR IMPLEMENTING HEALTHCARE FRAUD COUNTERMEASURES

This application is a continuation of U.S. Ser. No. 10/348,931 entitled SYSTEM AND METHOD FOR IMPLEMENTING HEALTHCARE FRAUD COUNTERMEASURES filed on Jan. 22, 2003 now U.S. Pat. No. 7,209,886 which is incorporated herein by reference.

BACKGROUND OF THE INVENTION

1. Field of the Invention

The present invention relates, in general, to systems and method for discouraging fraud, and, more particularly, to software, systems and methods for discouraging and preventing healthcare fraud.

2. Relevant Background

In the United States, for example, more than 4 billion health insurance benefit transactions are processed every year. These benefit transactions are handled by private health insurance plans as well as tax-funded insurance programs such as Medicare and Medicaid. Healthcare fraud is the deliberate submittal of false claims for reimbursement to these private health payers and public programs. In either case, society at large ultimately suffers from these loses of healthcare fraud through higher health insurance premiums, restricted benefits, higher taxes and higher insurance co-payments for privately and publicly insured patients.

Even though only a small percentage of these transactions are fraudulent, the total value of the losses caused by this fraud is staggering. The National Health Care Anti-Fraud Association reports that health care fraud resulted in theft of $1.3 trillion in calendar-year 2000 alone. On Feb. 21, 2002, the United States Department of Health and Human Services reported its finding that of the $191.8 billion in claims paid in 2001, 6.3 percent—amounting to $12.1 billion—should not have been paid due to erroneous billing or payment, inadequate provider documentation of services to back up the claims and/or outright fraud.

One of the largest single sources of health care fraud is dishonest health care providers (e.g., physicians, chiropractors, osteopaths, and alternative-medicine care givers). Although the vast majority of health care providers are honest, the dishonest minority are uniquely situated to conduct systemic, ongoing and broad scale fraud that has been, until now, difficult to detect and prove. For example, health care providers have access to patient identities and insurance/Medicare/Medicaid information of those patients, knowledge of the reimbursement processes, access to the provider reimbursement systems, and a familiarity with fraudulent claims that are difficult to detect.

A common fraud involves billing for services that were never rendered. This may involve using genuine patient information to fabricate entire claims or may involve padding claims with charges for procedures or services that did not take place. In a common scenario, a health care provider gains authority to perform a series of treatments over a period of time, then performs only some of the treatments while submitting reimbursement for the entire series. While current regulations require a patient signature indicating that services were performed, a dishonest provider often convinces the patient to sign these verification forms in advance. The patient may or may not be aware of the fraud. Currently, unless the patient discovers and informs the insurance company or government program that they did not receive the services, the fraud is difficult to detect.

The existence of dishonest providers harms the vast majority of honest providers in that all providers are subject to increased scrutiny, more complex forms, and allegations of fraud stemming from innocent mistakes in handling claims. As a result, fraud creates a chilling effect on all honest care providers that desire to give their patients the best care possible. This chilling effect impacts courts, regulatory agencies, and the legal system as well as the existence of fraud creates a cloud of doubt around all people who submit or prosecute claims for health care reimbursement on behalf of victims of accidents, on-the-job injuries, and other legitimate reimbursable claims.

The current response to healthcare fraud involves creating criminal and civil penalties for abuse. While such steps are necessary, they have limited effect unless the fraud can be discovered and proven. Discovery is difficult and insurance companies and government agencies are expending greater and greater resources in anti-fraud processes. More recently, "whistleblower" programs are being used to encourage fraud reporting by patients themselves. However, because patients implicitly trust their healthcare providers and often lack the sophisticated knowledge to detect fraud, these programs have limited effect.

Technological solutions have been proposed that involve collecting data about healthcare transaction and using data mining and sophisticated matching techniques to identify some types of fraud. While such systems can be useful in detecting some fraud such as double billing, over prescription, and the like, they are not generally useful to detect all fraud relating to submission of claims for services that have not been provided. These solutions rely on databases that hold detailed information about patients and medical histories of those patients. New regulations under the health insurance portability and privacy act make it more difficult or impossible to collect and use such information.

Accordingly, a need exists for systems, methods, and software that discourage and prevent healthcare fraud.

SUMMARY OF THE INVENTION

Briefly stated, the present invention involves a system that uses biometric information unique to an individual combined with location information to create a persistent record indicating that a particular person was physically present at a particular place. Specifically, the present invention provides methods of discouraging healthcare fraud in conjunction with providing a health care service to a patient in which the patient provides a biometric signature. An event record is created where the event record creates an association between the biometric signature, a patient identifier, and location information indicating a location at which the biometric signature is obtained. The event record is stored in a central data store and can be later retrieved to verify the patient was present at the location. In terms of deterring health care fraud, the invention makes it significantly more difficult to submit claims for healthcare services that were not provided and significantly easier to detect a variety of fraudulent or erroneous reimbursement practices.

DETAILED DESCRIPTION OF THE PREFERRED EMBODIMENTS

Figure 1:
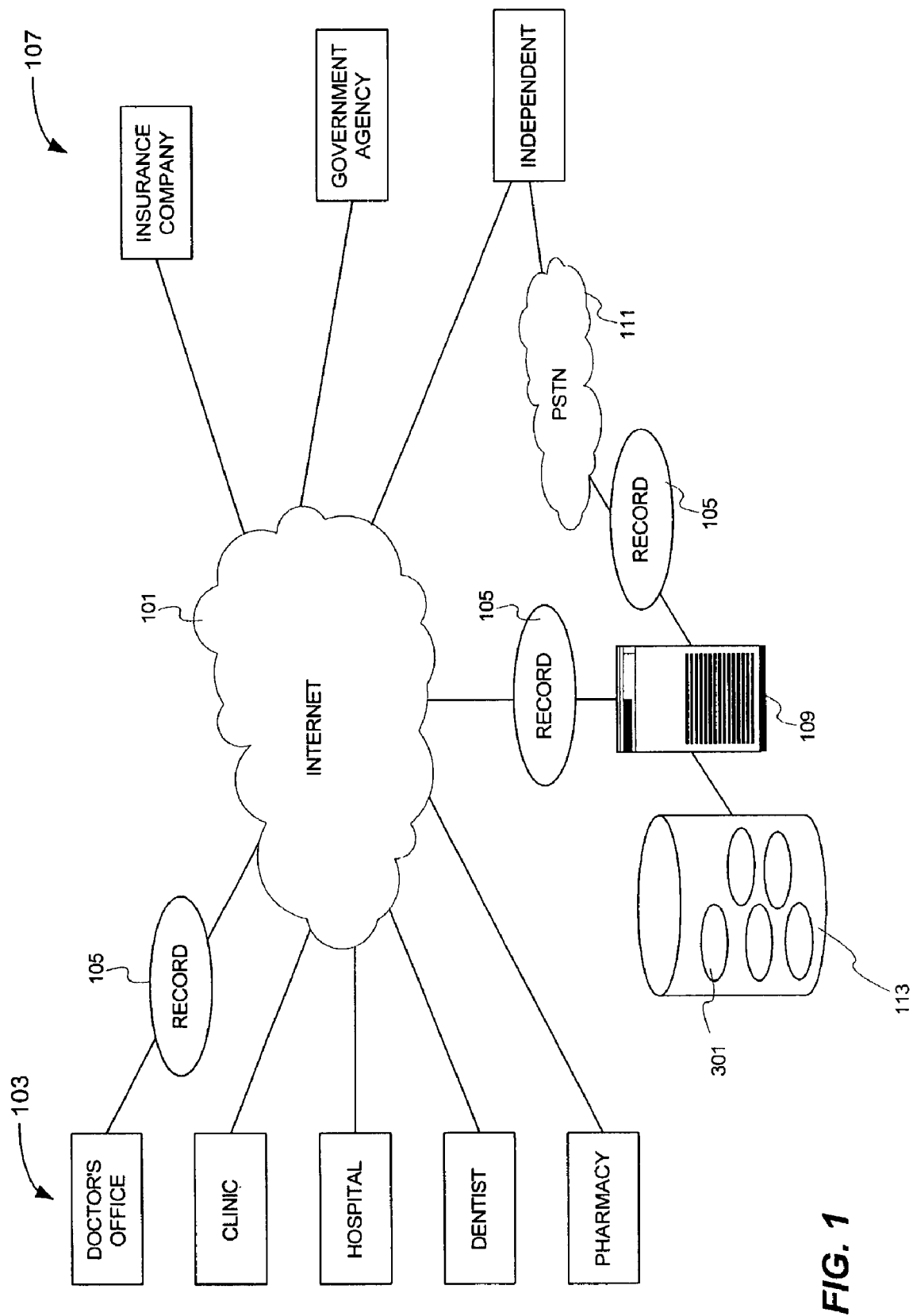
FIG. 1 shows a networked computer environment in which the present invention is implemented.

In a particular implementation, the present invention involves a system that uses biometric information unique to an individual to verify that a patient is physically present at a place of treatment (i.e., in a health care providers office). Biometric systems have been used to identify and authenticate individuals in a variety of contexts. These systems, for example, create a database containing biometric information about a plurality of known or authorized individuals. Prior to performing a service for the individual, a fingerprint scan, or other biometric signature, of an individual is taken and the scan information is used to access the database. The database returns other information such as the individual's name, photograph, signature, or the like that can be used to authenticate the identity of the individual.

Unlike these prior systems, however, the present invention is not primarily concerned with identifying an individual or authenticating that an individual is who he/she represents himself/herself to be. While the present invention could operate in conjunction with such systems, such operation is not required. Instead, the present invention desires to create a record, called an "event record", that records that a particular individual was at a particular location at a particular time. This simple record does not require a database of authorized users or sophisticated matching algorithms to correlate biometric information with stored biometric records, although the biometric information obtained by the present invention may also be used in conjunction with these identification/authorization systems. Unlike prior systems, the event record is preserved in a database for future reference should it be necessary to validate the individuals presence at a particular location.

The present invention is illustrated and described in terms of a distributed computing environment such as an enterprise computing system using public communication channels such as the Internet. However, an important feature of the present invention is that it is readily scaled upwardly and downwardly to meet the needs of a particular application. Accordingly, unless specified to the contrary the present invention is applicable to significantly larger, more complex network environments as well as small network environments such as conventional LAN systems.

The present invention is described in terms of several specific implementations which use specific data record formats, data gathering devices, and protocols. It should be understood that, unless stated to the contrary, the present invention is readily modified and extended to use other formats, devices, and protocols that are available to a particular implementation. For example, fingerprint scanners are a widely available, cost effective biometric tool used in the specific embodiments, but any type of biometric signature may be used including face recognition, retinal scan, voice recognition, gait recognition, and the like, so long as the biometric technique generates a unique digital signature that can be captured and stored. Moreover, the present invention is particularly useful in discouraging healthcare fraud, but may be used in any application where it is desirable to create an auditable record of where an individual is at a particular time.

FIG. 1 shows an exemplary computing environment in which the present invention may be implemented. Environment includes a plurality of entities that are coupled by a data communication network such as Internet 101 and/or public switched telephone network 111. It should be understood that any available network technology such as local area network (LAN) and wide area network (WAN) technology may suitable to implement communication network 101 in particular applications. As shown in FIG. 1, the present invention provides a system and method for implementing data communications between various healthcare service providers 103 and payer entities 107 that provide insurance reimbursement for healthcare services. Health care providers 103 include, for example, physicians, clinics, hospitals, dentists, pharmacies, and the like. Health care providers 103 may include any type of traditional or alternative medicine, physical therapy, nutritional support, and mental health care that are available.

In accordance with the present invention, each health care provider 103 is associated with an identifiable physical location at which patients or clients receive services. When a patient or client visits the health care provider location, one or more records 105 of that visit, called "event records", are generated and transferred to event record archive services 109. Various types and formats of event records 105 are contemplated by the present invention, but an important record type includes biometric signature information of the patient, a unique identification of the healthcare provider 103, and a timestamp indicating when the patient visited the healthcare provider 103.

Payer entities 107 have obligations to reimburse health care providers 103 for certain claims when services are provided to insured patients. Currently, payers 107 essentially reimburse all claims made by health care providers 103 on the assumption that all of these claims are valid absent some indication of dishonesty. Because of the complexity of both the insurance industries and the health care services industry, detecting fraud has been difficult.

In accordance with the present invention, central event storage services entity 109 retains and archives records 105 in a data store 113. In a particular example, these records are maintained on a patient-by-patient basis and include an auditable history of visits by a patient to one or more health care providers 103 including the date and time of such visits. Using this information, a particular claim for reimbursement can be readily correlated to a particular record to verify that a patient was at least present at the health care provider's location at the time the services were rendered. In some implementations the event storage services 109 will provide information to appropriate payer entities so that claims management software processes implemented by the payer 107 can be used to verify claims. In other implementations event storage services 109 will implement the validation processes. In yet other implementations, event storage services 109 acts as a clearinghouse to validate claims before they are submitted to payers 107. In yet other implementations, requests for validation and/or transfer of records 105 can be handled over PSTN 111 using either data or voice communication channels. The selection of the particular implementation or group of implementations can be readily altered to meet the needs of a particular application.

Figures 2, 3:
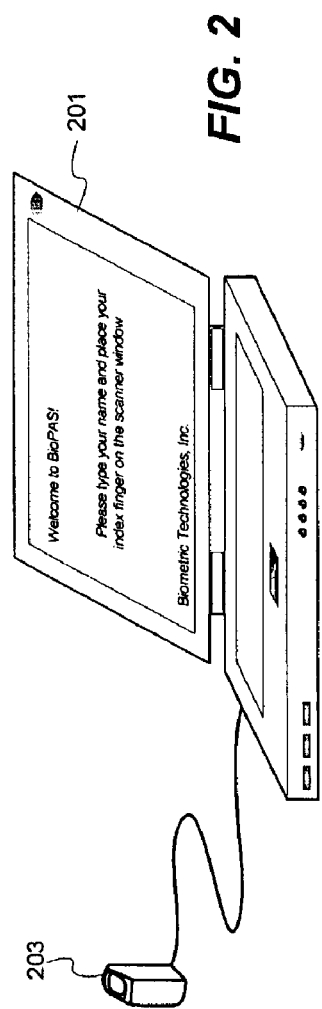
FIG. 2 shows an exemplary patient interface station that may be used in a health care providers location in an implementation of the present invention.
FIG. 3 illustrates an embodiment of a patient record in accordance with the present invention.

As shown in FIG. 2, each health care provider 103 location is outfitted with computing hardware and software that implements a patient interface 201. Patient interface may be implemented as a stand-alone system or integrated with existing practice management software used to record patient appointments, patient records and/or handle patient billing or other office tasks. In many health care provider locations it is common to have a patient log-in or sign-in that is used each patient visit to notify the health care provider of the patients arrival, and similarly operated by the provider's staff to note the patient's departure. These systems are good candidates for integration with the present invention.

Patient interface 201 is coupled to or includes a biometric signature device 203. In the particular implementation this device comprises a fingerprint scanner such as a "hamster" sold by SecuGen Biometric Solutions of Milpitas, Calif. or a Morphotouch by Sagem Morpho, Inc. in Tacoma, Wash. However, the present invention is largely vendor independent and a number of alternative fingerprint scanning devices are available. Moreover, biometric signature device 203 is readily implemented using any available device that is capable of generating a unique signature based on the physical presence of a person at the patient interface 201. In the case of a fingerprint scanner, biometric signature device 203 outputs a binary sequence of a preselected length (e.g., 128-byte or 512-byte, etc.) that is referred to as the fingerprint minutia.

Patient interface 201 desirably includes mechanisms to reliably determine a date/time at which the biometric signature was captured. This is readily implemented by a system clock in a conventional computer system, or by obtaining clock signals from external sources. In some implementations the patient interface includes mechanisms and software for providing location information. The location information can be fixed in the patient interface in the form of a stored value, such as the health care providers identification number. Alternatively, this information can be provided by geographic locating systems such as the global positioning system (GPS) and the like.

Patient interface 201 uses this biometric signature to generate one or more types of messages. Patient interface 201 implements two important types of transactions in a particular invention. Initially, a patient is enrolled or registered to initiate creation of a patient record with event storage system 109 using an "enrollment record" 501 shown in FIG. 5. A similar record can be used to update patient information in a patient record stored in event storage system 109. Subsequently, patient visits result in an "event record" 601 shown in FIG. 6 that is used to update the patient record with event storage system 109. In one implementation, the event record transports the biometric signature (e.g., the fingerprint minutia) to central event storage 109 so that any processing of the biometric signature occurs at event storage system 109 rather than within patient interface 201. Alternatively, the patient interface 201 requests reference biometric signature information from event storage system 109 which enables processing of the biometric signature to be performed in a distributed fashion at the health care provider location.

Patient interface 201 includes, for example, processes to prompt the patient to identify himself/herself and operate the biometric signature device 203. The patient identification may involve typing or speaking a name, ID number, social security number, insurance identification, or some other information that is substantially unique to the patient. Alternatively, the biometric signature can itself be used to identify a patient, although such an implementation involves somewhat more complex technologies in that the signature needs to be matched against a database of biometric signatures to distinguish the patient.

An enrollment transaction can be initiated automatically or semi-automatically in response to determining that a patient record does not exist. In this case the patient is prompted using interface 201 to provide additional information such as date of birth, address, phone number, insurance information and the like to meet the needs of a particular application. The biometric signature and other information gathered are packaged into a data packet containing appropriate header/trailer information and a command code indicating a particular transaction (i.e., enrollment or update). The data packet may be implemented as an XML document in a particular implementation. The formed record is transferred, using encryption if desired, to event storage system 109.

Figures 4, 5, 6:
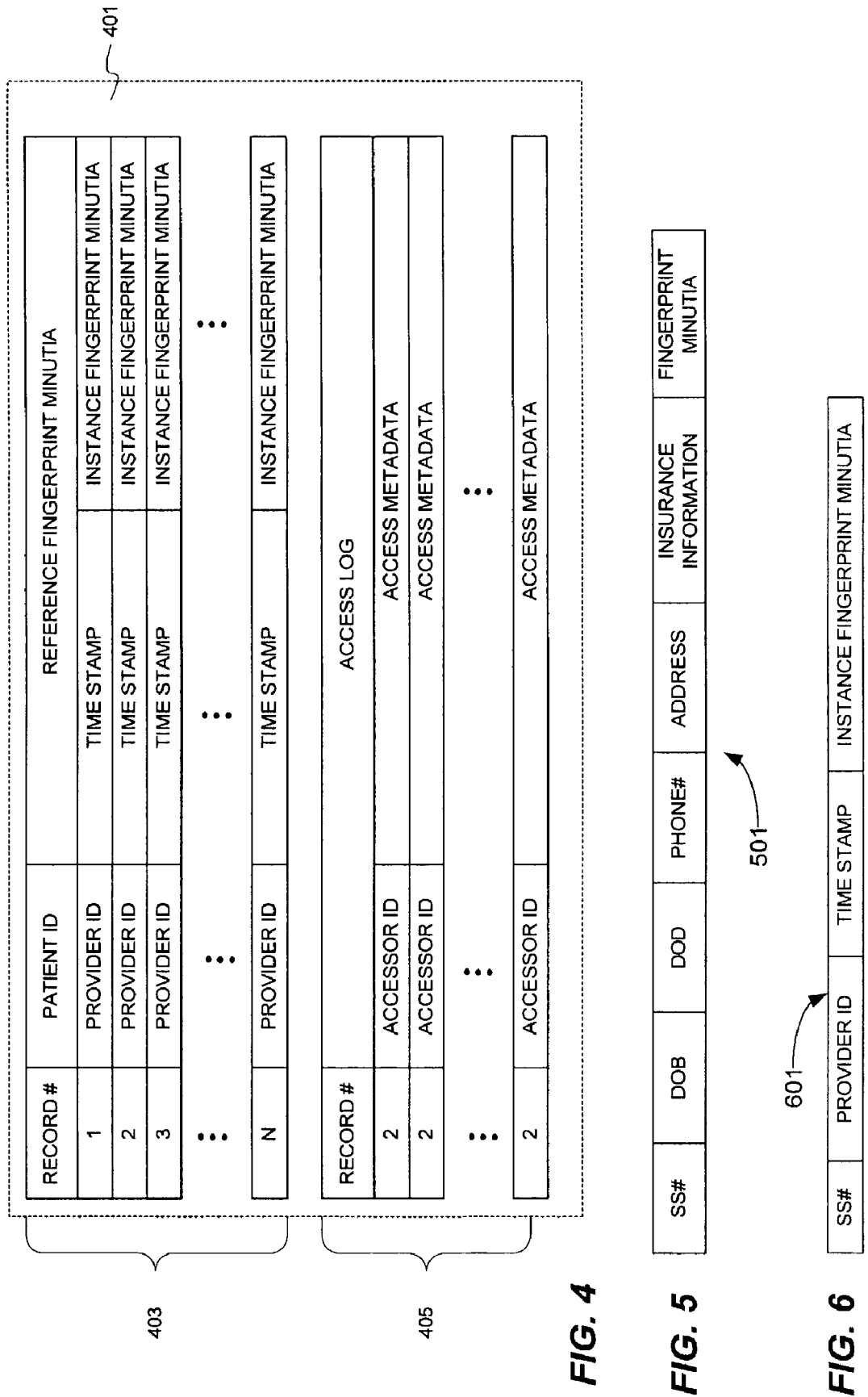
FIG. 4 illustrates an alternative embodiment of a patient record in accordance with the present invention.
FIG. 5 is an exemplary information set used for an initial enrollment operation in accordance with the present invention.
FIG. 6 is an exemplary information set used to record a particular patient event in accordance with an embodiment of the present invention.

FIG. 3 and FIG. 4 illustrate two alternative types of patient records 301 and 401, respectively, that are useful in the practice of the present invention. Patient records 301 and 401 comprise persistent data records stored in data store 113 event storage system 109. It should be understood that FIG. 3 and FIG. 4 present conceptual representations of a patient records and that particular hardware and/or database management systems will typically determine the physical implementation of the data structure. However the data structures shown in FIG. 3 and FIG. 4 depict the relationships between information intended by the present invention. Also, the records 301 and 401 can be augmented with any type and variety of additional information to meet the needs of a particular application.

Record 301 comprises a first portion 303 that includes patient identification information and a number of entries where each entry refers to a specific patient visit. The patient ID field comprises unique information about the patient such as social security number, date of birth, address, an assigned ID number, phone number, insurance information, and the like. In a simplified example, each patient record 301 contains a unique social security number that is used to access the patient record 301.

In the embodiment of FIG. 3 patient record 301 includes a reference fingerprint minutia. This reference minutia is compared to the minutia included with incoming event records 105 to determine matches which indicate that the patient that generated the event record 105 is verified to be the same person associated with the patient record 105. The plural entries each contain sufficient information to indicate each time a patient has visited a given provider. Any number of entries may be included in a patient record 313.

Patient record 301 also includes a lower portion 305 that serves as an access log or journal. Portion 305 comprises an arbitrary number of entries where each entry identifies an event entry from the portion 303, and records access information such as when and who requested access to a particular entry within patient record 301. In particular implementations the entries in lower portion 305 may include various metadata describing the access request that might record individual credentials of the person causing the access, command codes indicating the nature of the request (e.g., read or modify), and/or a purpose code indicating to what use the information would be used. This log/journal information can be used later to verify and demonstrate the integrity of the data.

The embodiment of FIG. 4 is substantially similar, but differs from that of FIG. 3 in that each entry in upper portion 403 includes a persistent record of the fingerprint minutia for a particular event record 601. Although storage requirements may be increased significantly, the actual fingerprint minutia can be accessed at any time and compared against a given person's to prove authoritatively that a patient record 405 belongs to a particular individual, and to demonstrate the whereabouts of that individual as represented by event entries stored in upper portion 403. Log/journal portion 405 is substantially identical to log/journal portion 305 described hereinbefore.

Figure 7A:
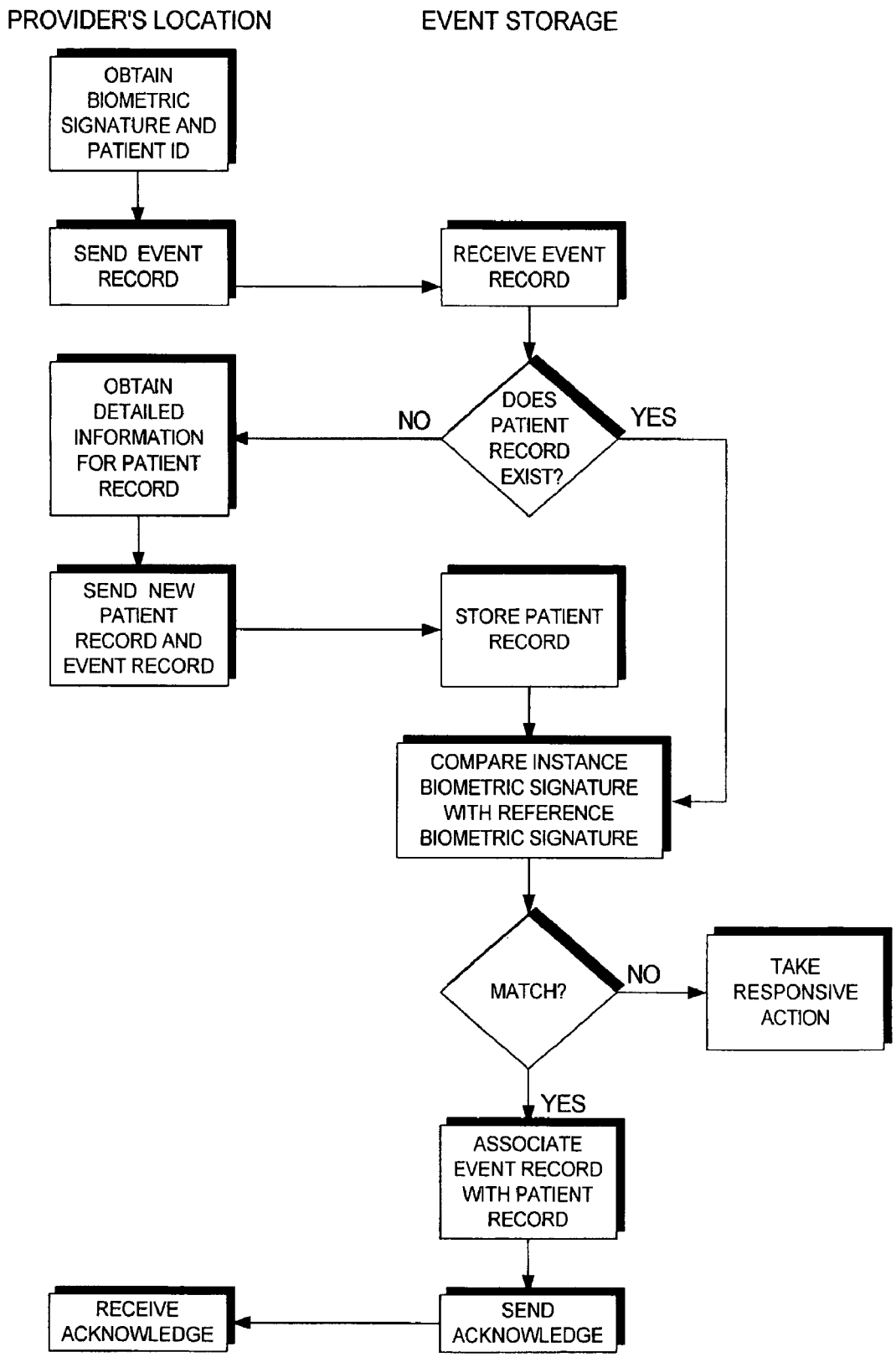
FIG. 7 illustrates in simplified flow-diagram form front-end processing activities in a particular embodiment.

FIG. 7A shows important activities in "front-end" processing used to enroll patients and gather event records in accordance with an embodiment of the present invention. At a healthcare provider's location, a patient is instructed or prompted to operate patient interface 201 so as to obtain a biometric signature. Additionally, the patient may be prompted to provide other identification information such as an ID number, name, social security number and the like. This information is compiled into an event record, which is transmitted to event system 109.

Event storage system 109 uses the event record information to identify a patient record 301/401 that corresponds to the event record. For example, where patient records 301/401 are indexed by social security number, the social security number information in an event record can be used to identify a particular patient record. In cases where the patient records 301/401 are indexed by fingerprint minutia, the fingerprint minutia within an event record is to identify a particular patient record. When it is determined that a record exists, the present invention initiates processes that update the patient record with a new entry that records the patient visit to the health care provider 103.

When it is determined that a patient record does not exist, the present invention requests additional detailed information that is desired to establish a new patient record 301/401. Patient interface 201 implements processes to obtain the desired information, and generates an enrollment message 601 back to event storage system 109. Event storage system 109 creates the new patient record, and updates the new patient record to reflect the current event record information (i.e., provider identification, timestamp, and the like). Optionally, the event storage system 109 will send an acknowledgement message to the patient interface to confirm that the patient record has been successfully updated. This acknowledgement message can be used to generate a receipt of some kind for a patient. In the event an acknowledgement message is not received, patient interface 201 may cache the particular request for later handling.

Figure 7B:
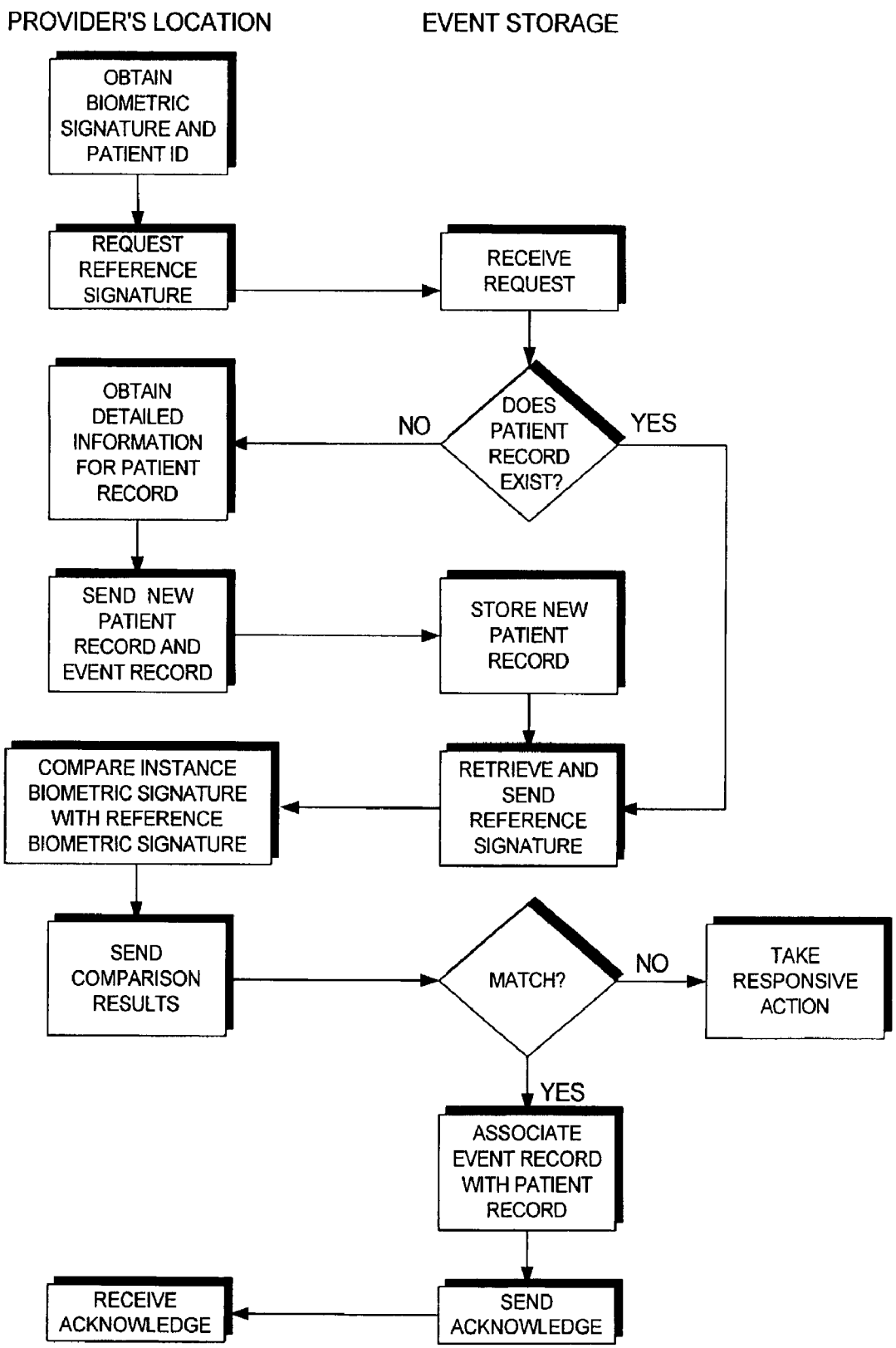

FIG. 7B shows activities in an alternative "front-end" processing system used to enroll patients and gather event records. An important difference in comparison to the embodiment of FIG. 7A is that in the embodiment of FIG. 7B, matching the "instance" biometric signature to a reference biometric signature occurs in processes executing at the healthcare provider location rather than in the central event storage system 109. This enables the workload involved in matching biometric signatures to be distributed out amongst the many participating healthcare provider systems, freeing resources in event storage system 109. The provider system then informs event storage system 109 whether a match was determined, and the biometric signatures can be destroyed in the provider's system.

In either the embodiment of FIG. 7A or FIG. 7B the system may use any available matching algorithm to determine a suitable match between the captured biometric signature and a reference biometric signature. These algorithms, often supplied with the biometric device 203, may produce a binary (i.e., yes/no) output, or may produce a variable output reflecting a degree of confidence in the match. In the vast majority of cases, once a patient is enrolled subsequent visits to a health care provider will result in a match between a captured biometric signature and the reference signature. In response to this match, the event record information is added to the patient record at central event storage system 109.

In some instances a biometric signature that is captured will fail to match the reference biometric signature for a particular patient identification. This can occur when, for example, the patient identification value is entered incorrectly. This can also occur when the person supplying the biometric signature is not operating the device 203 properly. In these cases, a failure to match results in a responsive action such as prompting the patient to re-enter identification information or to repeat the actions involved in capturing a biometric signature. When these actions are re-performed, it can be once again determined whether a match exists.

Of course, in some instances a captured biometric signature will fail to match a reference record because the human being that is submitting the captured biometric signature is different from the human being that submitted the reference record. In such a situation, although a higher likelihood of fraud exists, the present invention does not attempt to notify a health care provider or restrict access to the health care services. Instead, an event record is created that indicates the variance or exception condition to signify that a match was not found. An event record with an exception condition recorded will readily indicate a reimbursement claim that should be treated with special attention.

In some cases it is valuable to be able to verify that a patient was not only present at the healthcare provider's location, but also that the patient was present for a certain amount of time. For example, if a treatment should require thirty minutes to perform, the patient will be present for the entire thirty minutes. In these cases, a patient may be prompted to submit biometric signature data at the beginning and ending of a visit, or at several times during the visit when appropriate. The visit is then recorded by multiple event records, or by a single event record that indicates a time during the visit as well as an extent of time for the visit. Although such an implementation is a slight imposition on the patient, it creates a greater disincentive to fraud. Moreover, such data can be used to detect new types of fraud such as a practice of submitting claims for a complex treatment when in fact a simpler procedure was used. Also, event records for a given health care provider can be audited to determine whether claims are being submitted for multiple patients who were being treated at the same time, or for submitting multiple claims where the aggregate time spent providing treatment is greater than the actual time spent at the health care facility.

Significantly, because it is contemplated that the healthcare services will be provided whether or not an acknowledge is received, it is acceptable to delay transmission of event records and/or enrollment records to well after the patient visit. In contrast, some prior systems that condition providing services upon receiving an authentication of the patient become extremely dependent on receiving an acknowledgment in real time. Further, because it is contemplated that the healthcare services will be provided whether or not a biometric signature match is determined, the present invention is very robust in response to errors, delays, equipment failures and communication difficulties that might otherwise interfere with a time-sensitive decision as to whether care should be provided.

FIG. 8 through FIG. 11 illustrate four exemplary process flows for handling the "back-end" or reimbursement transactions using the biometric techniques in accordance with the present invention. To simplify illustration and understanding, FIG. 8 through FIG. 9 operate from an assumption that a patient has been enrolled. In such cases, a patient visit to a health care provider involves generating a new event record, which is transmitted to event storage system 109 and used to update an existing patient record 301/401.

In each of the embodiments shown in FIG. 8 through FIG. 11, claims for reimbursement arriving from the various providers are validated by matching to an event record for a particular patient from event storage system 109. Payment is made to the appropriate provider for validated reimbursement claims. In some instances an event record corresponding to the claim for reimbursement will not exist, or the matching event record will include information that a variance or exception condition existed when the matching the biometric signature provided at the time of service with the patient's reference biometric signature. In such instances, the payer will likely require additional investigation and a situation-dependent response to paying the reimbursement claim.

Figure 8:
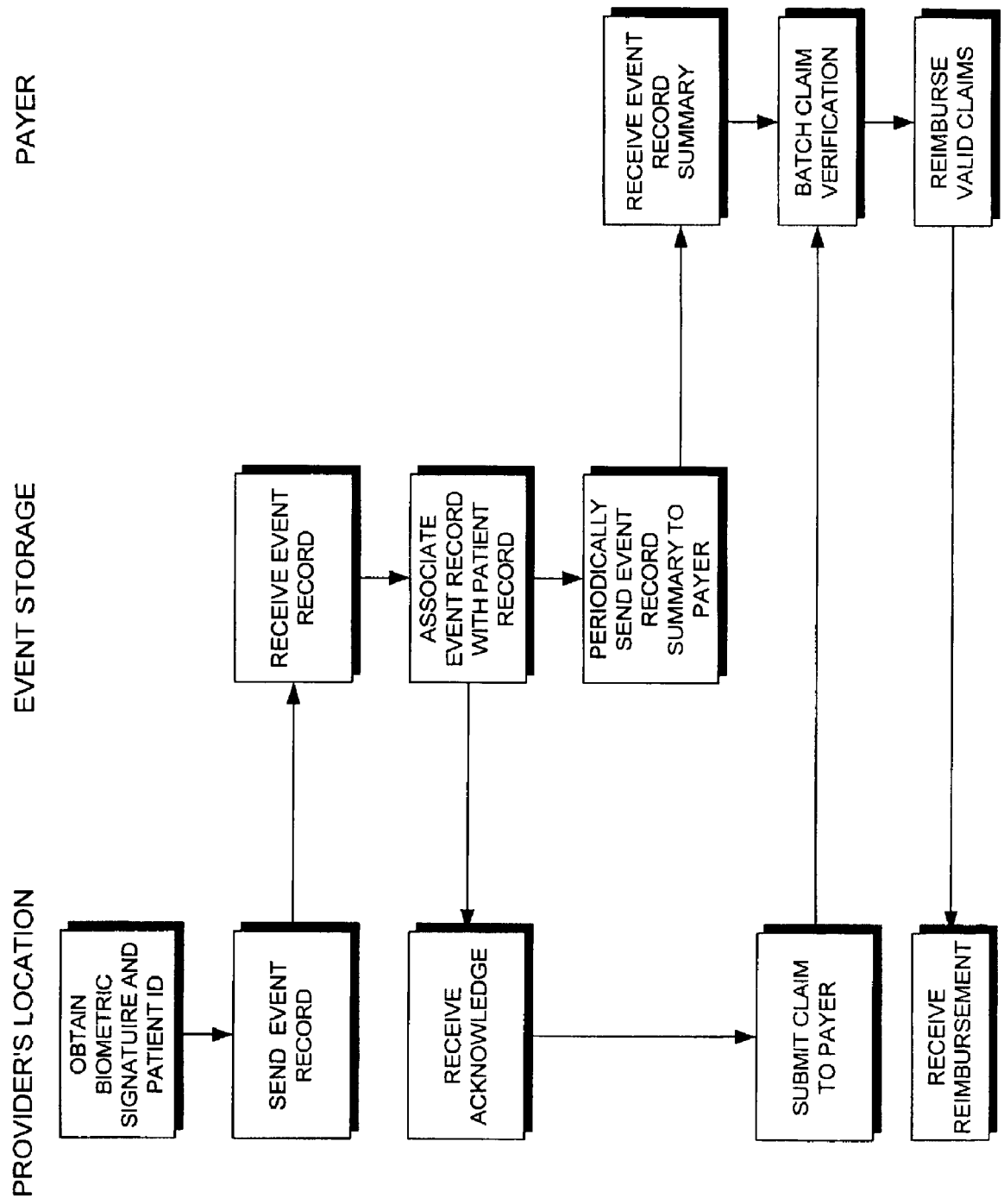
FIG. 8 through FIG. 11 show alternative back-end claims processing events in accordance with various embodiments of the present invention.

In the first model shown in FIG. 8, event storage system 109 periodically generates batch summary reports for each subscribing payer entity (e.g., insurance company, government agency, and the like). These reports include information indicating when each covered patient visited a health care provider. In this model, the payer entity takes responsibility for matching these recorded patient visits to submitted claims using any available matching algorithms.

Figure 9:
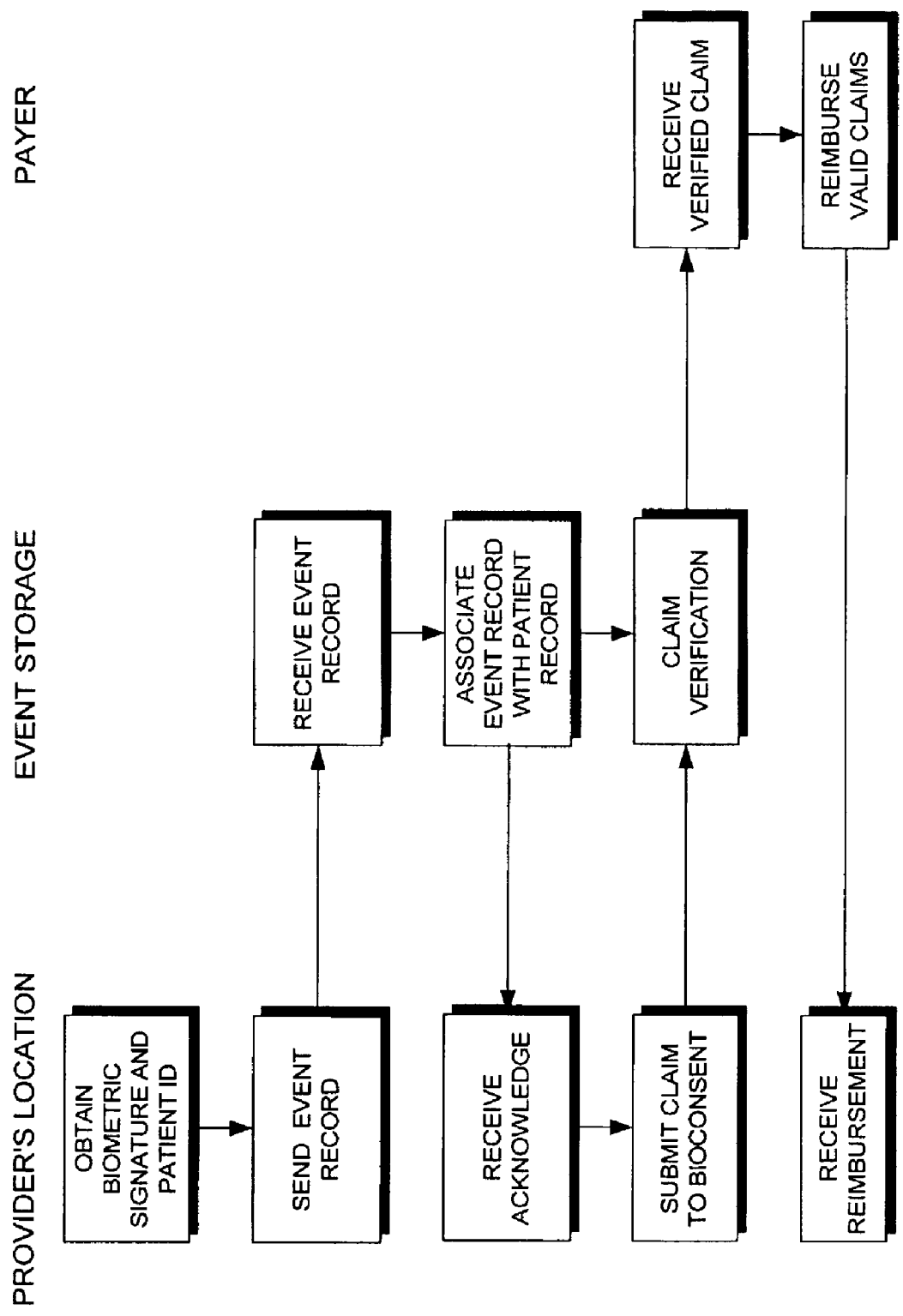

In the second model shown in FIG. 9, event storage system 109 is used to verify claims from health care providers before they are submitted to a payer entity. In this manner, the payer entity can operate with a high degree of assurance that the claims they are processing are valid. At the same time, the payer entity does not need to modify their own systems and software as claim verification processes are implemented by event storage system 109. Optionally, event storage system 109 provides summary reports indicating claims that were not validated so that the payer entity can follow up with further investigation.

Figure 10:
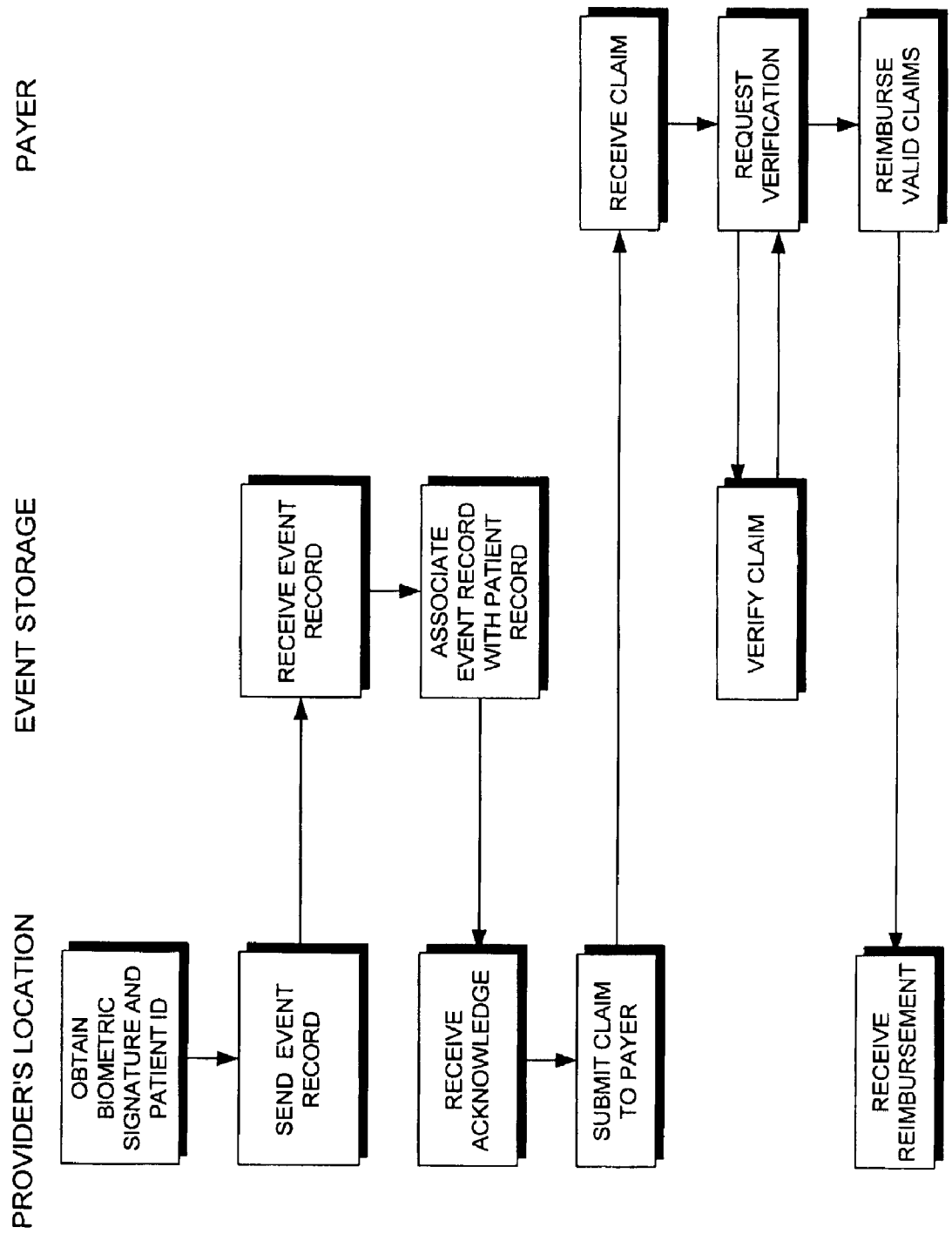

In the third model shown in FIG. 10, event storage system 109 acts as a clearinghouse by validating claims one at a time or in small groups. In this implementation providers deal with payers in a substantially conventional fashion. Upon receipt of a claim the payer will request verification either by sending a verification request such as an XML message, or by an automated phone system similar to that used to obtain credit card authorizations. Event storage system 109 can handle validation of these requests very quickly in most cases as the requests are typically small and the database lookup involved is simple. This also ensures that the payer is using fresh data with up-to-the-minute collection of event records in each patient record 301/401.

Figure 11:
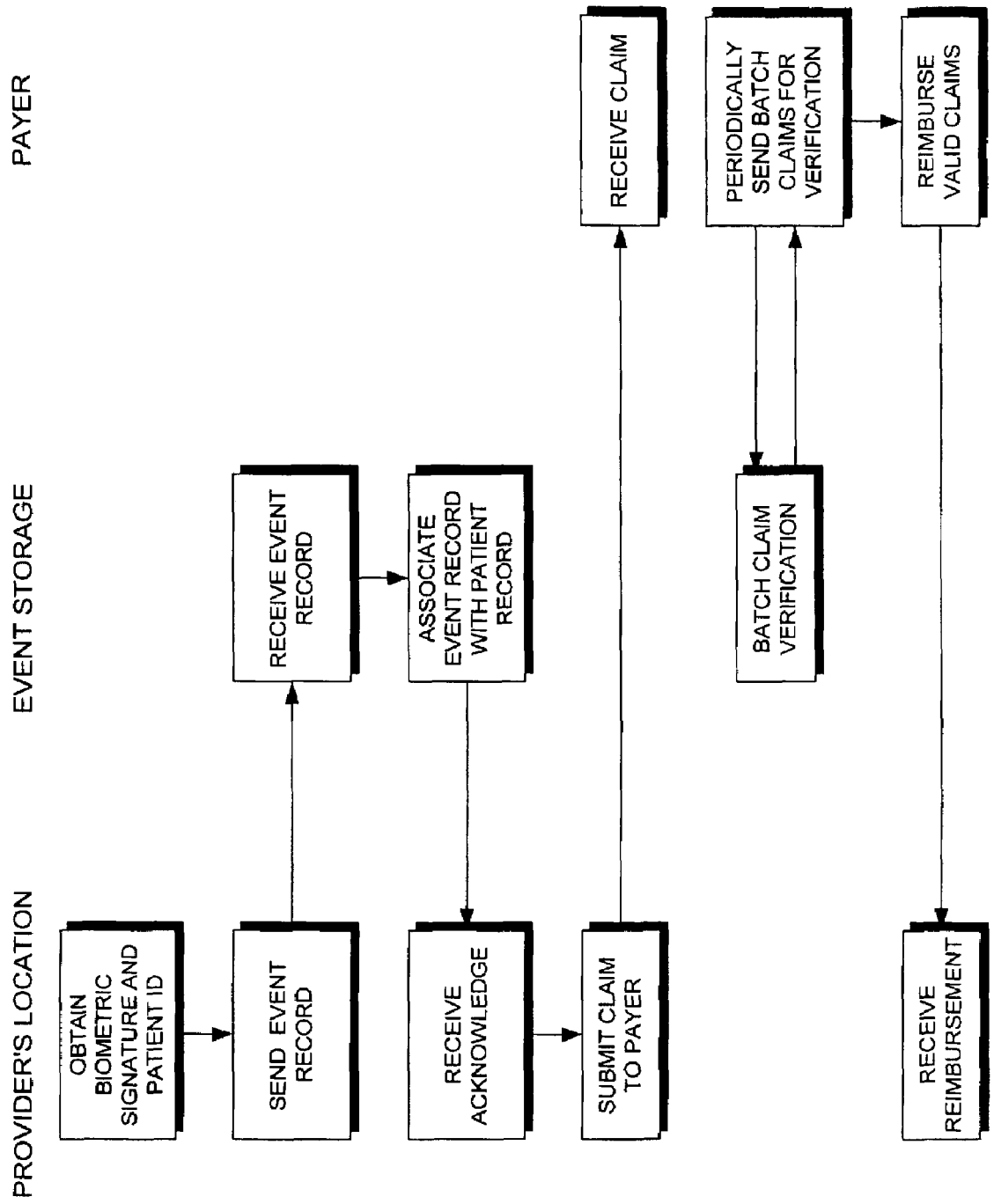

In a fourth model shown in FIG. 11, event storage system 109 periodically receives batch claim reports from each subscribing payer entity. Like the model shown in FIG. 9 and FIG. 10, event storage system 109 is responsible for validating claims, however, the embodiment of FIG. 11 allows this verification to occur in batch processes which may be more efficient than one-at-a-time processing. Event storage system 109 can provide a batch response indicating yes/no information for each claim. In actuality, event storage system 109 need only provide a list of claims that are not validated as the payer entity can assume any other claims are validated.

The systems and methods of the present invention have broad applicability outside of the health care claims processing industry. In a sense, the present invention can be used like a watchman's clock to create a record that verifies the location of a particular person at a particular location and time. There is a growing problem, for example, in government provided services such as child protective services and parolee monitoring caused by government officials that fail to visit their wards when they are supposed to. The present invention is readily implemented in a handheld device in which the time and location of a meeting with a protected child, for example, can be recorded by scanning the fingerprint of the child. This system would operate to verify meetings with parolees or other persons for which there is a responsibility to monitor. These devices can be readily integrated with location devices and software, such as global positioning systems, to provide information about the location of such meetings.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed.

The invention claimed is:

1. A method of discouraging phantom billing healthcare fraud comprising:
    providing a health care service;
    in conjunction with providing said health care service at a particular location to a patient, causing said patient to provide a biometric signature;
    capturing said biometric signature;
    creating an event record that records said patient was at said particular location at a particular time and/or date, said event record consisting of a patient identifier, said biometric signature, and location information indicating said particular location at which said biometric signature is obtained and at which said health care service is provided and said event record indicates the absence of phantom billing, wherein said event record is created using a computer system;
    storing said record in a computerized data store, wherein said record corresponds to reimbursement information and said location information in said record provides evidence that a particular patient was at a suitable location for providing said healthcare services;
    providing an interface to said computerized data store wherein said interface receives said reimbursement information and determines whether a record in said computerized data store matches said reimbursement information;
    determining whether said record corresponds to said reimbursement information wherein the absence of a positive match indicates a phantom bill;
    indicating to a payer entity whether said particular patient was at a suitable location for providing said healthcare services based on said determination.

2. The method of claim 1 further comprising making a reimbursement decision by said payer entity using said information related to said event record.

3. The method of claim 1 further comprising storing said event record in a computerized data store.

4. The method of claim 1 further comprising obtaining a biometric signature at least twice during said provision of health care services.

5. The method of claim 1 further comprising:
    receiving a claim for reimbursement for said health care services;
    retrieving one or more event records corresponding to said health care services from said data store;
    matching said claim for reimbursement to an event record for a particular patient to determine whether said one or more event records indicate that said patient was at a suitable location for reimbursing said health care services; and authorizing financial reimbursement of said health care service based in part upon said determination that said patient was present at a location suitable for reimbursing said health care service.

6. The method of claim 1 further comprising:

retrieving one or more records from said data store; and performing a fraud detection process using said retrieved records.

7. The method of claim 1 wherein said biometric signature comprises a fingerprint record.

8. The method of claim 1 wherein said location information comprises an identification code assigned to a heath care facility.

9. The method of claim 1 wherein said location information comprises a network address of a computer used to obtain said biometric signature.

10. The method of claim 1 wherein said location information comprises a device address of a fingerprint scanner.

11. A biometric audit trail system comprising:

means for causing a patient to provide a biometric signature on a date and at a location where the health care service is provided;

means for capturing said biometric signature;

means for creating a record that records said patient was at said location at a particular time and/or date, said record comprising a patient identifier, said biometric signature, location information indicating said particular location at which said biometric signature is obtained;

means for storing said record in a computerized data store, wherein said record corresponds to reimbursement information and said location information in said record provides evidence that a particular patient was at a suitable location for providing said healthcare services;

means for providing an interface to said computerized data store wherein said interface receives said reimbursement information and determines whether a record in said computerized data store matches said reimbursement information;

means for determining whether said record corresponds to said reimbursement information wherein the absence of a positive match indicates a phantom bill;

means for indicating to a payer entity whether said particular patient was at a suitable location for providing said healthcare services based on said determination.

12. The system of claim 11 further comprising processes operable to analyze said retrieved biometric records to identify patterns amongst a plurality of biometric records.

13. The system of claim 11 wherein said biometric record further comprises a timestamp indicating a time and/or date at which said biometric information was obtained.

14. A method of discouraging phantom billing healthcare fraud comprising:

providing a health care service;

in conjunction with providing said health care service at a particular location to a patient, causing said patient to provide a biometric signature;

capturing said biometric signature;

creating an event record that records said patient was at said particular location at a particular time and/or date, said event record consisting of said biometric signature and location information indicating said particular location at which said biometric signature is obtained and at which said health care service is provided wherein said event record is created using a computer system;

storing said record in a computerized data store, wherein said record corresponds to reimbursement information and said location information in said record provides evidence that a particular patient was at a suitable location for providing said healthcare services;

providing an interface to said computerized data store wherein said interface receives said reimbursement information and determines whether a record in said computerized data store matches said reimbursement information;

determining whether said record corresponds to said reimbursement information wherein the absence of a positive match indicates a phantom bill;

indicating to a payer entity whether said particular patient was at a suitable location for providing said healthcare services based on said determination.

15. A method of discouraging phantom billing healthcare fraud comprising:

providing a health care service;

in conjunction with providing said health care service at a particular location to a patient, causing said patient to provide a biometric signature;

capturing said biometric signature;

creating an event record that records said patient was at said particular location at a particular time and/or date, said event record consisting of said biometric signature and at least one timestamp indicating a time and/or date at which said biometric signature is obtained and at which said health care service is provided and said event record indicates the absence of phantom billing, wherein said event record is created using a computer system;

storing said record in a computerized data store, wherein said record corresponds to reimbursement information and said location information in said record provides evidence that a particular patient was at a suitable location for providing said healthcare services;

providing an interface to said computerized data store wherein said interface receives said reimbursement information and determines whether a record in said computerized data store matches said reimbursement information;

determining whether said record corresponds to said reimbursement information wherein the absence of a positive match indicates a phantom bill;

indicating to a payer entity whether said particular patient was at a suitable location for providing said healthcare services based on said determination.

16. A method of discouraging phantom billing healthcare fraud comprising:

providing a health care service;

in conjunction with providing said health care service at a particular location to a patient, causing said patient to provide a biometric signature;

capturing said biometric signature;

creating an event record that records said patient was at said particular location at a particular time and/or date, said event record consisting of a patient identifier, said biometric signature, at least one timestamp, and location information indicating said particular location at which said biometric signature is obtained and at which said health care service is provided wherein said event record is created using a computer system;

storing said record in a computerized data store, wherein said record corresponds to reimbursement information and said location information in said record provides evidence that a particular patient was at a suitable location for providing said healthcare services;

providing an interface to said computerized data store wherein said interface receives said reimbursement information and determines whether a record in said computerized data store matches said reimbursement information;

determining whether said record corresponds to said reimbursement information wherein the absence of a positive match indicates a phantom bill;

indicating to a payer entity whether said particular patient was at a suitable location for providing said healthcare services based on said determination.

17. A method of discouraging phantom billing healthcare fraud comprising:

providing a health care service;

in conjunction with providing said health care service at a particular location to a patient, causing said patient to provide a biometric signature;

capturing said biometric signature;

creating an event record that records said patient was at said particular location at a particular time and/or date, said event record consisting of a patient identifier, said biometric signature, at least two timestamps indicating a range of times at which said health care service was provided, and location information indicating said particular location at which said biometric signature is obtained and at which said health care service is provided and said event record indicates the absence of phantom billing, wherein said event record is created using a computer system;

storing said record in a computerized data store, wherein said record corresponds to reimbursement information and said location information in said record provides evidence that a particular patient was at a suitable location for providing said healthcare services;

providing an interface to said computerized data store wherein said interface receives said reimbursement information and determines whether a record in said computerized data store matches said reimbursement information;

determining whether said record corresponds to said reimbursement information wherein the absence of a positive match indicates a phantom bill;

indicating to a payer entity whether said particular patient was at a suitable location for providing said healthcare services based on said determination.

18. A method of discouraging phantom billing healthcare fraud comprising:

providing a health care service;

in conjunction with providing said health care service at a particular location to a patient, causing said patient to provide a biometric signature;

capturing said biometric signature;

creating an event record that records said patient was at said particular location at a particular time and/or date, said event record consisting of a patient identifier, said biometric signature, metadata, and location information indicating said particular location at which said biometric signature is obtained and at which said health care service is provided and said event record indicates the absence of phantom billing, wherein said event record is created using a computer system;

storing said record in a computerized data store, wherein said record corresponds to reimbursement information and said location information in said record provides evidence that a particular patient was at a suitable location for providing said healthcare services;

providing an interface to said computerized data store wherein said interface receives said reimbursement information and determines whether a record in said computerized data store matches said reimbursement information;

determining whether said record corresponds to said reimbursement information wherein the absence of a positive match indicates a phantom bill;

indicating to a payer entity whether said particular patient was at a suitable location for providing said healthcare services based on said determination.

19. A method of discouraging phantom billing healthcare fraud comprising:

providing a health care service;

in conjunction with providing said health care service at a particular location to a patient, causing said patient to provide a biometric signature;

capturing said biometric signature;

creating an event record that records said patient was at said particular location at a particular time and/or date, said event record consisting of said biometric signature, location information, and at least one timestamp indicating a time and/or date at which said biometric signature is obtained and at which said health care service is provided, wherein said event record is created using a computer system;

storing said record in a computerized data store, wherein said record corresponds to reimbursement information and said location information in said record provides evidence that a particular patient was at a suitable location for providing said healthcare services;

providing an interface to said computerized data store wherein said interface receives said reimbursement information and determines whether a record in said computerized data store matches said reimbursement information;

determining whether said record corresponds to said reimbursement information wherein the absence of a positive match indicates a phantom bill;

indicating to a payer entity whether said particular patient was at a suitable location for providing said healthcare services based on said determination.

20. A method of discouraging phantom billing healthcare fraud comprising:

providing a health care service;

in conjunction with providing said health care service at a particular location to a patient, causing said patient to provide a biometric signature;

capturing said biometric signature;

creating an event record that records said patient was at said particular location at a particular time and/or date, said event record consisting of said biometric signature, location information indicating a location at which said biometric signature is obtained and at which said health care service is provided, wherein said event record is created using a computer system;

storing said record in a computerized data store, wherein said record corresponds to reimbursement information and said location information in said record provides evidence that a particular patient was at a suitable location for providing said healthcare services;

providing an interface to said computerized data store wherein said interface receives said reimbursement information and determines whether a record in said computerized data store matches said reimbursement information;

determining whether said record corresponds to said reimbursement information wherein the absence of a positive match indicates a phantom bill;

indicating to a payer entity whether said particular patient was at a suitable location for providing said healthcare services based on said determination.

21. The method of claim 1 wherein said act of storing said event record is performed before said biometric signature is used to identity said patient receiving said healthcare services.

22. The method of claim 1 wherein said act of storing said event record is performed before said biometric signature is used to authenticate said person receiving said healthcare service.

* * * * *